United States Patent [19]

Sancoff et al.

[11] Patent Number: 5,105,983
[45] Date of Patent: Apr. 21, 1992

[54] INFUSION APPARATUS

[75] Inventors: Gregory E. Sancoff, Leucadia; Frederic P. Field, Cardiff, both of Calif.

[73] Assignee: Block Medical, Inc., Carlsbad, Calif.

[21] Appl. No.: 429,313

[22] Filed: Oct. 31, 1989

[51] Int. Cl.⁵ .............................................. B65D 35/28
[52] U.S. Cl. .................................... 222/103; 222/95; 222/105; 222/214; 222/215; 222/386.5; 417/478
[58] Field of Search .............. 222/95, 103, 105, 173, 222/207, 209, 213, 215, 527, 386.5, 212, 380, 214, 183, 129, 131, 182; 604/212, 214, 259, 262, 250, 132, 133, 131; 417/478, 479; 251/4, 10

[56] References Cited

U.S. PATENT DOCUMENTS

| 515,288 | 2/1894 | Harsin | 604/132 |
|---|---|---|---|
| 920,250 | 4/1909 | Blakeslee | 222/214 |
| 1,392,601 | 10/1921 | Rose | 222/214 |
| 3,046,978 | 7/1962 | Leg | 417/478 |
| 3,412,906 | 11/1968 | Dinger | 222/183 |
| 3,468,308 | 9/1969 | Bierman | 128/214 |
| 3,469,578 | 9/1969 | Bierman | 128/214 |
| 3,486,539 | 12/1969 | Jacuzzi | 141/329 |
| 3,506,005 | 4/1970 | Bilio et al. | 128/214 |
| 3,883,046 | 5/1975 | Thompson et al. | 222/95 |
| 3,895,631 | 7/1975 | Buckles et al. | 128/213 |
| 3,945,539 | 3/1976 | Sossong | 222/386.5 |
| 3,961,725 | 6/1976 | Clark | 222/1 |
| 3,993,069 | 11/1976 | Buckles et al. | 128/214 |
| 4,085,865 | 4/1978 | Thompson et al. | 222/386.5 |
| 4,140,117 | 2/1979 | Buckles et al. | 128/213 |
| 4,201,207 | 5/1980 | Buckles et al. | 128/214 |
| 4,264,018 | 4/1981 | Warren | 222/386.5 |
| 4,318,400 | 3/1982 | Peery et al. | 128/214 |
| 4,386,929 | 6/1983 | Peery et al. | 604/132 |
| 4,419,096 | 12/1983 | Leeyer et al. | 604/132 |
| 4,452,473 | 6/1984 | Ruschke | 285/81 |
| 4,515,294 | 5/1985 | Udall | 222/214 |
| 4,597,758 | 7/1986 | Aalto et al. | 604/256 |
| 4,658,990 | 4/1987 | Ramage | 222/106 |
| 4,692,151 | 9/1987 | Blackman | 604/132 |
| 4,702,397 | 10/1987 | Gortz | 222/211 |
| 4,722,372 | 2/1988 | Hoffman et al. | 222/214 |
| 4,722,732 | 2/1988 | Martin | 604/132 |
| 4,741,733 | 5/1988 | Winchell et al. | 604/51 |
| 4,769,008 | 9/1988 | Hessel | 604/132 |

Primary Examiner—Kevin P. Shaver
Assistant Examiner—Philippe Derakshani
Attorney, Agent, or Firm—Baker, Maxham, Jester & Meador

[57] ABSTRACT

A liquid infusor apparatus includes an elastic sleeve mounted on an elongated member and within a spherical housing to enable it to expand naturally to maintain a constant pressure over the infusion period. An alternate embodiment includes a holding reservoir that may be pre-filled, and a pressure reservoir that is loaded from the holding reservoir preparatory to infusion.

16 Claims, 4 Drawing Sheets

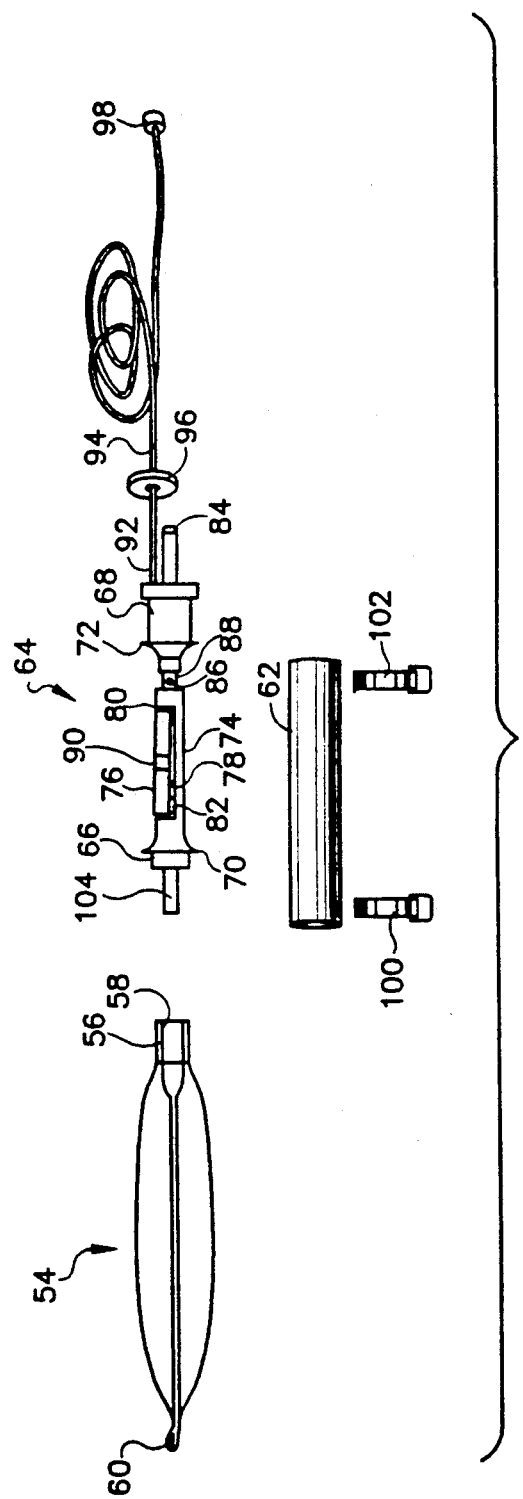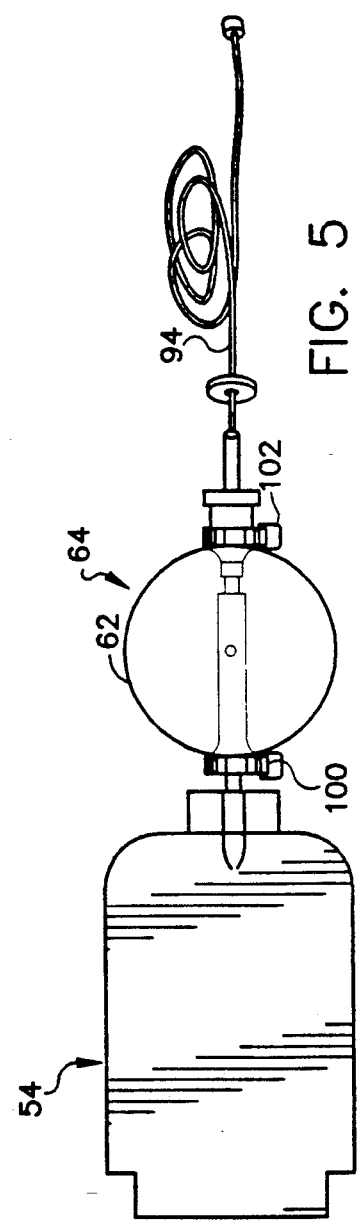

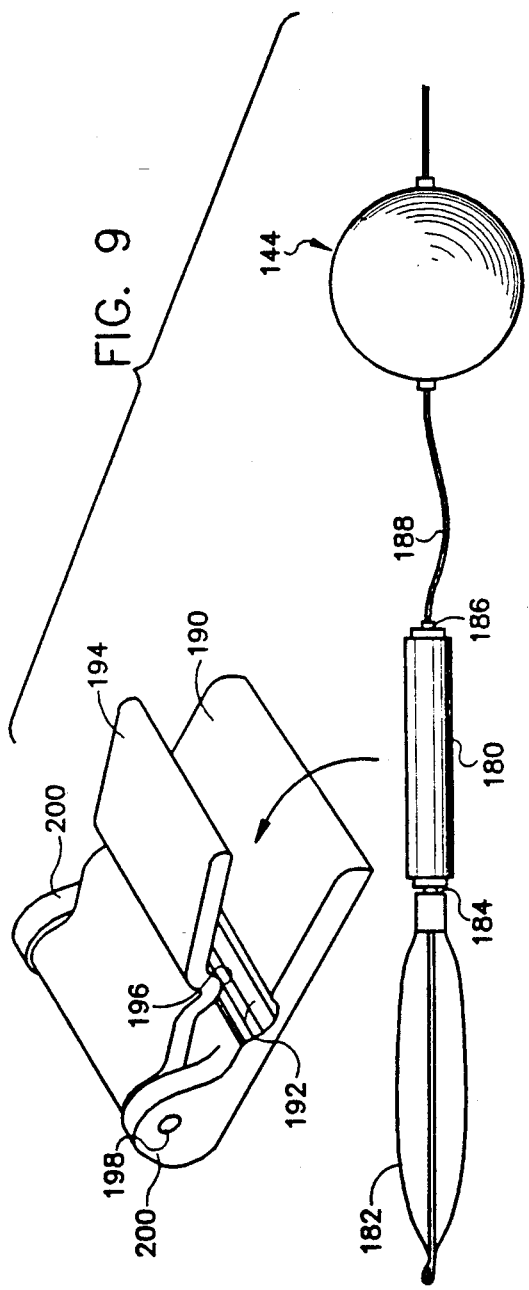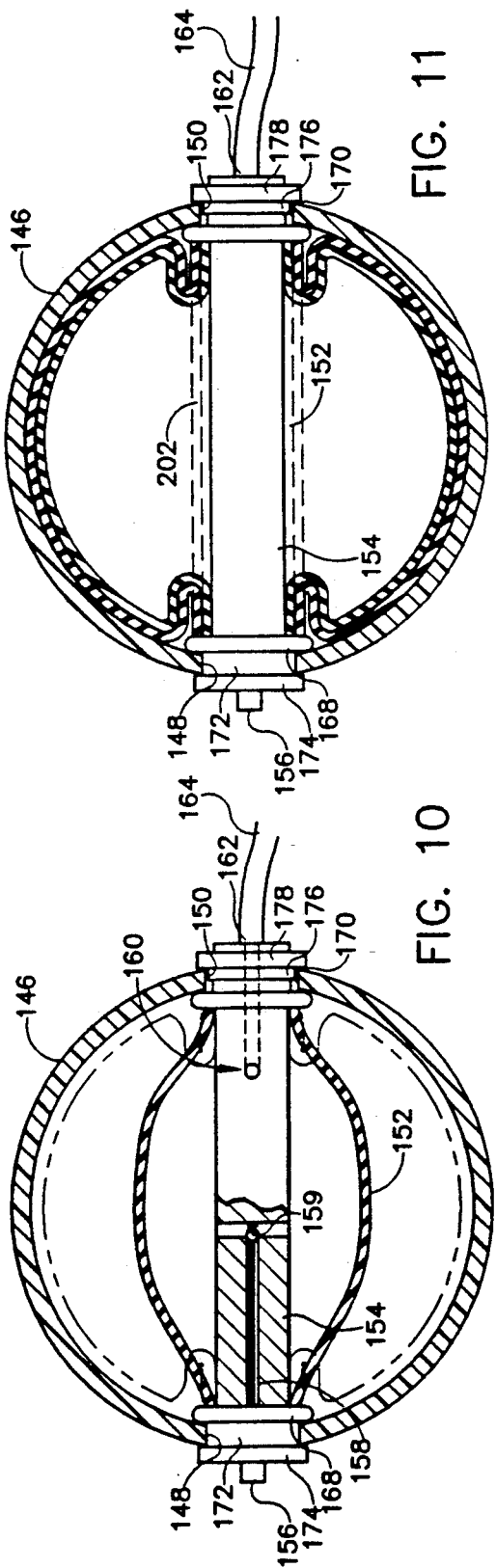

INFUSION APPARATUS

BACKGROUND OF THE INVENTION

The present invention relates to liquid dispensing apparatus and pertains particularly to an improved infusor apparatus for delivering intravenous drugs at a controlled rate to a patient.

It is often necessary to intravenously supply patients with pharmaceutically active liquids over a long period of time at a controlled rate. It is desirable that this be accomplished while the patient is in an ambulatory state. A few devices have been developed in the past for accomplishing this purpose.

The prior art devices typically comprise an elastic bladder forming a liquid container mounted in an elongated cylindrical housing, and having a flow control valve or device and tubing for supply of the liquid to the patient. The elastic walls of the bladder expand along the walls of the cylindrical housing when filled with the liquid, and provide the pressure for expelling the liquid. These prior art devices are typically filled by hand by means of a syringe which often require an inordinate amount of force.

Another drawback to the prior art devices is that the bladder is forced to expand into an unnatural elongated configuration along the housing walls as the container is filled. As a result of this unnatural configuration, the pressure of the bladder varies widely with the volume of liquid therein. Therefore, they do not have a reasonably stable pressure and flow rate over the infusion period.

Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

It is desirable that the pressure and flow rate be reasonably constant over the infusion period. It is also desirable that no abnormal pressures occur during the infusion.

Accordingly, it is desirable that an improved infusor apparatus be available.

SUMMARY AND OBJECTS OF THE INVENTION

It is the primary object of the present invention to provide an improved liquid infusor apparatus.

In accordance with a primary aspect of the present invention, a liquid infusor apparatus comprises an elastic reservoir mounted within a spherical chamber and enabled to expand naturally at a constant pressure. Another embodiment comprises a holding reservoir that may be pre-filled, and a pressure reservoir that is loaded from the holding reservoir preparatory to infusion.

BRIEF DESCRIPTION OF THE DRAWING

The above and other objects and advantages of the present invention will become apparent from the following description when read in conjunction with the accompanying drawings wherein:

FIG. 4 is an exploded view of the reservoir and nozzle assembly of the embodiment of FIG. 1;

FIG. 5 is a top plan view of the assembled components of FIG. 4;

FIG. 9 is a perspective exploded view of a further embodiment of the invention;

FIG. 10 is a side elevation view in section of the infusion pump of the embodiment of FIG. 9; and FIG. 11 is a view like FIG. 10 of a further modification of the embodiment of FIG. 10.

DETAILED DESCRIPTION OF A PREFERRED EMBODIMENT

Figure 1:
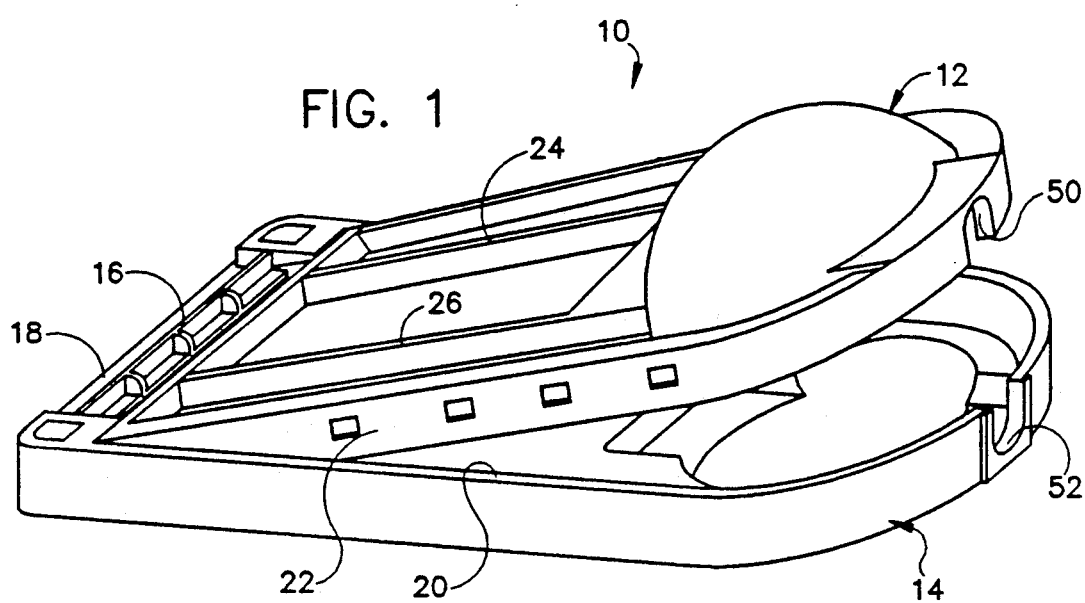
FIG. 1 is a perspective view of a housing assembly of a preferred embodiment of the invention.
Figure 2:
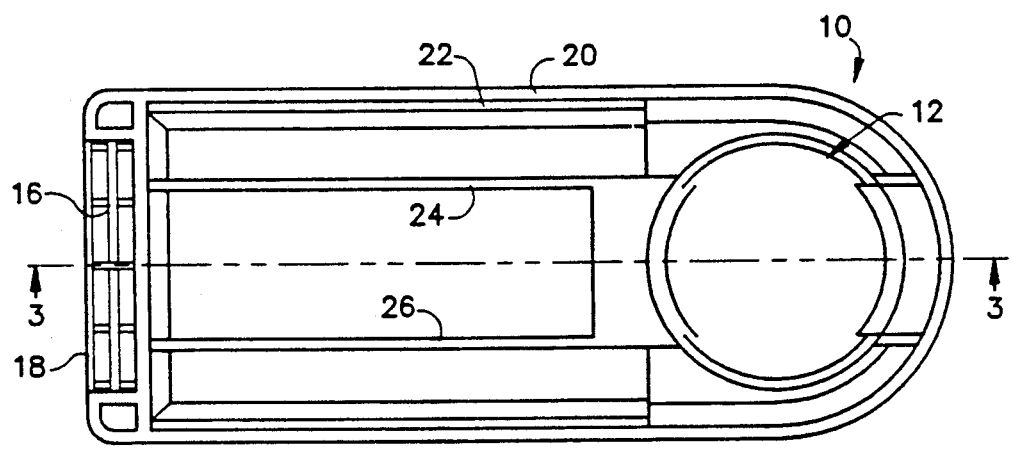
FIG. 2 is a top plan view of the embodiment of FIG. 1.
Figure 3:
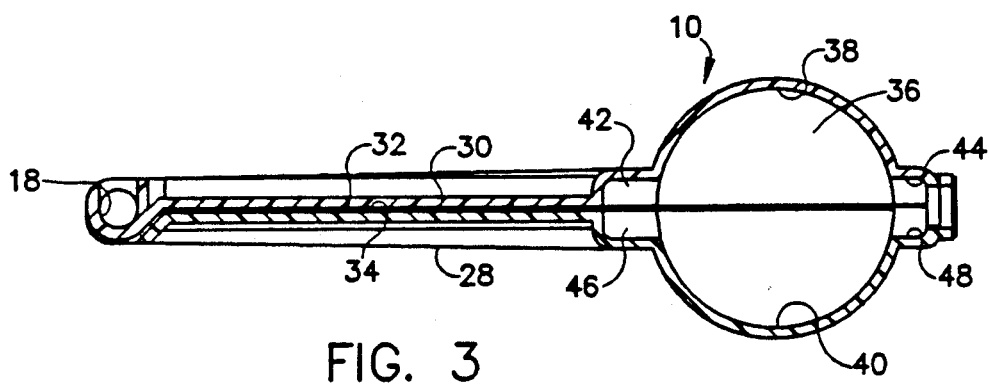
FIG. 3 is a view taken generally on line 3—3 of FIG. 2.

Referring to the drawings, and particularly to FIGS. 1-3, a preferred embodiment of a housing assembly for a preferred embodiment of the invention is illustrated. The illustrated housing comprises a pair of complementary half-shell like housings comprising essentially an upper housing 12 and a lower housing 14, hinged together at rear pivot axis by means of a built-in hinge pin 16 of the lower housing, and a U-shaped hinge journal 18 of the upper housing 12. The housings are essentially identical except for the hinge construction, and that the upper housing is constructed in the preferred form to fit within the inside of a peripheral rim 20 of the lower housing having a similar like rim 22.

The housing is preferably formed of a lightweight substantially rigid plastic, and formed to have a plurality of longitudinal reinforcing ribs 24 and 26 for the upper and lower housings. The housings fit together and form what can be considered a first or low volume cavity or chamber 30 between opposed surfaces 32 and 34, and a second high volume cavity or chamber 36 between upper semi-spherical surface 38 and lower semi-spherical surface 40. The housing is thus designed to accommodate a holding reservoir and a pressure reservoir as will be explained.

With reference to FIG. 3, the upper housing has recesses or cavities 42 and 44, with the lower housing having similar recesses or cavities 46 and 48 for accommodating the ends of a combination support and flow control unit, as shown in FIGS. 4 and 5, and as will be explained. Each housing is also provided with semi-circular cut-outs 50 and 52 at the forward end thereof for accommodating the forward or outlet end of the flow control unit.

Referring to FIGS. 4 and 5, a preferred form of reservoirs and control orifices is illustrated. As illustrated, a holding reservoir 54 comprises a generally flat one-hundred ten milliliter vinyl bag of a construction substantially like that of a typical I.V. bag. This includes a neck with an outlet port or opening 58 for attachment to a filler port of a pressure reservoir as will be explained. A bead or the like 60 on the tail end of the bag extends outside the space at the hinge of the housing to hold the bag in place in the chamber 30.

An elongated elastomeric membrane or tube 62 fits over and is clamped over an elongated generally cylindrical support member, designated generally by the numeral 64, which contains a one-way valve and the necessary flow control elements or implements. The elastomeric tube 62 is designed to form a pressure reservoir, and when pressurized, to inflate in a generally spherical configuration to fit within the spherical cavity 36 of the housing 10. The support member 64 includes a pair of end clamping surfaces 66 and 68, with adjacent annular shoulders 70 and 72 separating the clamping surfaces from the central nozzle assembly.

The central section of the support member includes a pressure damper, which comprises a generally cylindrical section 74 having a hinged lever or portion 76 formed by a slit 78, leaving a hinge portion or member 80. An elastomeric member 82 is positioned between the members 74 and 76 to bias against the final collapse of the elastomeric sleeve against lever 76, to eliminate a spike in pressure in situations where the elastomeric sleeve may be pre-stressed or stretched onto the support member.

The entire assembly has an inlet or fill port 84, which communicates by way of a passageway to a port 86 beneath an elastic band 88, forming a one-way valve for filling the elastic of pressure reservoir assembly. An outlet port 90 communicates by way of a passage in the support member 64 to an outlet port at 92 for connection and communication by way of tubing 94, which may include a filter 96 and orifice and cap assembly 98.

Upon assembly, the elastomeric tube 62 is preferably slide or slip fitted on the support member 64 between surfaces 66 and 68, and clamped in place by means of clamps 100 and 102. The member 62 is preferably slip fitted somewhat loosely with about one-thousandths (0.001) of an inch on support member 64, and not stretched either radially or longitudinally. The sleeve is constructed and mounted to accordion fold or roll a slight amount at both ends, as shown in FIGS. 10 and 11, to accommodate elongation when it is inflated. This slip or non-pressure fit of the elastomeric sleeve on the support member provides a naturally substantially uniformly expanding elastic pressure reservoir. It also eliminates a pressure spike as the reservoir approaches the near empty state in the discharge mode. This non-stressed fit also eliminates the need for the pressure damper previously described, elements 76–82.

In operation, the assembly is assembled as shown in FIG. 5 and placed within the housing of FIG. 1, with the housing in the partially open position as shown in FIG. 1. When it is desired to charge a pump for infusion, a pharmacist selects a predetermined quantity of a liquid medication to be administered, and loads it via port 84 into the holding reservoir. The liquid flows past the one-way valve 88 from port 86, and flows into the space 78 and into the bag 54 by way of port 104. This fills the bag 54 as illustrated in FIG. 4. In the alternative, he may select pre-filled bags of medication.

The outer housing is retained in its partially opened position, as shown in FIG. 1, until it is desired to pressurize the liquid for administration. Once the nurse or other attendant is ready to connect the I.V. (intravenous set), the housing 10 is closed by pressing the upper housing 12 and the lower housing 14 together, with the housing locking into the closed position. This action, as can be seen in FIG. 3, forces all liquid from the holding reservoir 54 into the pressure reservoir 62, which expands into a spherical configuration within the chamber 36. The elastic sleeve, in its preferred slip fit mode, applies an essentially constant pressure over its range back to its relaxed or empty state. This expanded or inflated elastic sleeve pressurizes the liquid, which then flows via port 90 along passage 78 and by way of outlet 92 along the tube 94 into the patient. The elastic bladder 62 continues to apply a pressure to the liquid, forcing it to flow via the orifices and passage for injection into the bloodstream of the patient.

When a stretched sleeve modification is used, and the pressure chamber is substantially empty, such that the sleeve contacts members 74 and 76, the member 76 yields under the pressure of the elastomeric member 62 by compressing elastomeric member 82, thus preventing a spike in pressure on the last quantity of fluid ejected from the elastic pressured system.

Figure 6:
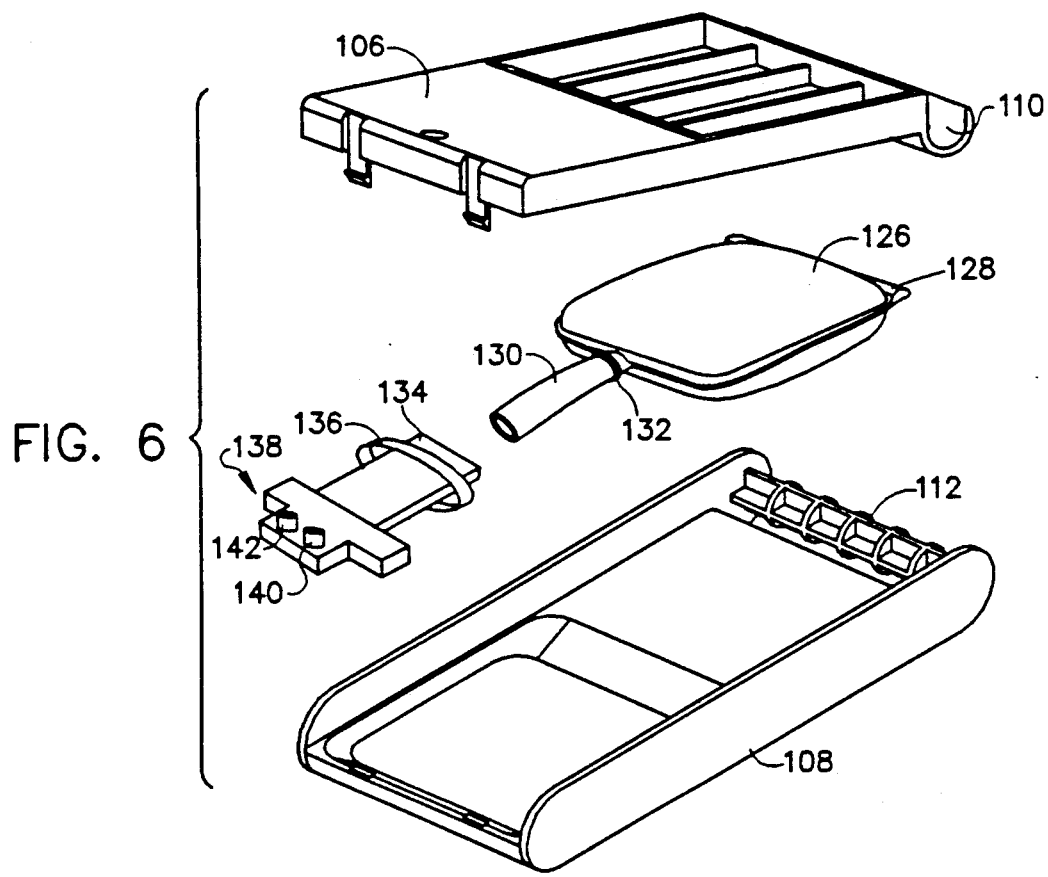
FIG. 6 is a perspective exploded view of an alternate embodiment of the invention.
Figure 7:
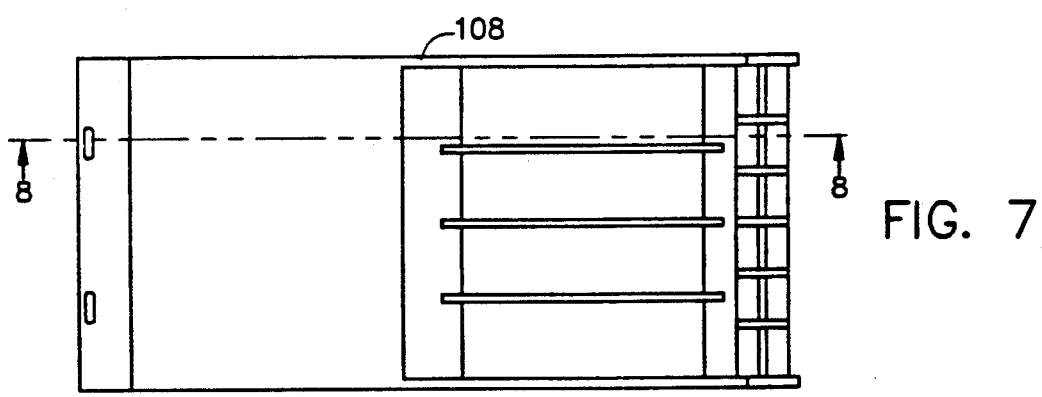
FIG. 7 is a top plan view of the embodiment of FIG. 6.
Figure 8:
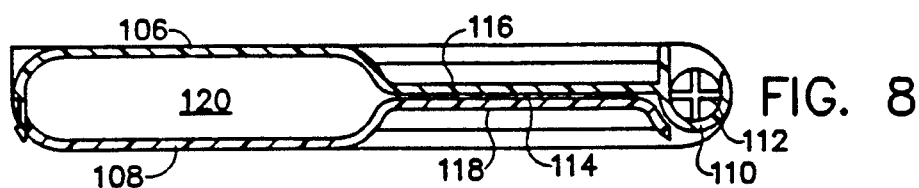
FIG. 8 is a section view taken generally along line 8—8 of FIG. 7.

Referring to FIGS. 6–9, an alternate more compact embodiment is illustrated wherein overall pump unit is of a generally flat rectangular configuration. Referring to FIG. 6, the overall assembly is illustrated in a perspective exploded view, showing upper and lower complementary half housings 106 and 108 of a somewhat similar construction as the prior embodiment, with a hinge assembly formed of a hinge journal 110 on the upper member, and a hinge pin 112 on the lower housing member. The upper and lower housings, when assembled together, form a low or essentially no volume chamber 114 between upper and lower planar faces 116 and 118 as in the prior embodiment for receiving a flexible holding reservoir. An adjacent larger or higher volume chamber 120 is formed between an upper cavity 122 and a lower cavity 124 for receiving an elastic or pressure reservoir.

This forms a housing having first and second chambers for receiving a bladder assembly substantially as in the prior embodiment. However, in a preferred form, a flat rectangular 110 ml. holding reservoir is formed by a 110 ml. vinyl bag 126, having a retainer strip or fold 128 as in the prior embodiment. An elastic or elastomeric tubular membrane 130 is connected at one end 132 to the neck of the bag 126.

A generally flat rectangular mandrel member 134, having a generally flat rectangular configuration, extends into the elastomeric tube 130 to aid in forming the bladder in its desired configuration, as well as voiding it to a zero volume, such that all liquid medication is expelled therefrom. At the forward end of the mandrel member, a valve assembly is formed, including a nozzle assembly with a fill port 140 for filling the holding reservoir, and a dispensing nozzle 142 to which the disposable I.V. tubes, as in the prior embodiment, are connected.

The pressure chamber formed by elastomeric member 130 is preferably shaped and configured to expand substantially uniformly within the chamber 120, such that a substantially uniform pressure is applied to the liquid over the length of the injection. A tubular elastic membrane tends to expand into a substantially spherical configuration. However, it has been determined that it can be preformed and shaped to substantially expand somewhat uniformly to conform to when guided by the generally rectangular cavity or chamber, as illustrated. This configuration provides a desirable compact configuration. However, a more uniform pressure on the liquid medication over the injection range is desirable.

Referring now to FIGS. 9 and 10, there is illustrated a still further embodiment of the infusor pump assembly, wherein the infusor pump is separable from the charging or filler pump. Moreover, it may be filled by any suitable means, such as a syringe or any other pressurizing means. As illustrated in FIG. 10, an infusor pump substantially like the previous embodiment, particularly the pump of FIG. 1, is designated generally by the numeral 144 and comprises an outer spherical housing of a size to accommodate the necessary volume of intravenous fluid to be pumped.

The housing 146 has a spherical configuration and is provided with coaxial, or more particularly aligned bores or ports 148 and 150, in which is mounted a bladder assembly comprising an elongated latex rubber elastic sleeve 152 mounted on an elongated central cylindrical support member 154. The central support member is preferably of a generally cylindrical configuration, and includes an inlet port 156 communicating by means of a passage 158 including a one-way valve 159, with the interior of the membrane 152. Any suitable check valve may be used to permit uncoupling of the filling unit without leakage of fluid from the pressurized bladder. An outlet passage 160 communicates via an outlet port and suitable valve and coupling assembly 162, with an intravenous feeding tube 164. The outlet coupling and valve assembly is preferably the well known type known as a luer lock. The luer lock has a valve that closes the outlet port when the outlet line 164 is uncoupled therefrom. The coupling is effective to open the outlet valve when coupled to the outlet fitting. Such luer locks are well known off-the-shelf items for I.V. delivery systems.

The latex tube or membrane 152 is mounted on the cylindrical support member 154 preferably in a slightly snug but un-stretched radial fit, and essentially relaxed elongated or non-stretched longitudinal fit. The elastic sleeve preferably has what shall be called a slip fit on the support member. This slip fit is preferably with a clearance of on the order of about one-thousandths of an inch of the sleeve on the support. This provides a non-stretched fit with essentially zero volume of the pressure chamber when in the non-stretched or totally relaxed mode. The ends of the elastic sleeve are sealingly clamped or secured to the support member, such as by means of suitable clamps or O-rings 168 and 170. These may extend to and cooperate with clamp sleeves 172 having a radial flange 174 and 176 having a radial flange 178. The clamp sleeves 172 and 176 may be used to position and mount the support member 154 in the housing 146.

The pressure applied by the pressure chamber will be substantially a function of the thickness of the wall of the elastic sleeve. For example, a typical two to three (2-3) psi may be obtained by a wall thickness of about eighteen to twenty-thousandths (0.018-0.020) of an inch. In order to obtain higher pressure with superior uniformity, a multi-layered sleeve configuration has been found to be preferred.

As illustrated in FIG. 11, a plurality of sleeves (two illustrated) 152 and 202 are slip fitted (non-stretched) on the support member. The inner sleeve 152 is slip fitted on the support member 154, and a second sleeve 202 is slip fitted over the first sleeve 152. These are shown in the full or fully inflated condition and inflated in phantom. These multiple layers have been found to be superior to the use of thicker membranes to obtain higher pressures. The multiple sleeves will roll or fold over at the ends, as illustrated, and like the single layer as illustrated in FIG. 10. Thus, to double the pressure, two sleeves of the same thickness are used.

When being filled, the elastic sleeve membrane 152 has a tendency to elongate, but expands into a spherical configuration (FIGS. 10 and 11). The sleeve is shown in the partially filled position in FIG. 10 and in the fully filled position in phantom. The elongation is accommodated in this pump configuration by an accordion effect at the ends of the tube, as shown in phantom, wherein the tube rolls over the ends thereof and inward along the support member 154 as it expands outward to fill the housing 146. The accommodation of the elastic membrane in the spherical configuration enables it to expand and contract in its natural fashion, and to maintain a substantially constant pressure and thereby pump rate over the intravenous injection period.

The layered or multiple sleeve configuration (FIG. 11) has been found to better accommodate the accordion fold and maintain a more uniform pressure than a thicker sleeve. The tubular elastic membranes are selected and mounted on the support member in a manner that enables them to roll or fold over at the ends when being filled.

The entire assembly includes a fill pump, which as shown in FIG. 9, comprises an elongated cylindrical collapsible tube 180 capable of springing back to its original shape, with enough force to draw fluid from a supply bag 182, preferably of a typical construction.

The pump has a suitable inlet check valve and coupling 184 at the inlet end, and an outlet valve and coupling 186 at the outlet end connected to a filler tube 188 coupled to the inlet port of the infusor pump 144.

A pump actuator for the assembly includes a base plate 190 of a generally rectangular configuration, with a semi-cylindrical recess 192 for receiving the tube member 180. A hand actuated lever member 194 includes a semi-cylindrical surface 196 complementary to the recess 192. The lever member 194 is pivotably connected at one end by suitable pins 198 to hinge members 200 at each side of the plate assembly.

This assembly forms a convenient fill apparatus for a pharmacist to use to fill the infusor pump 146. The housing of the pump 146 prevents its overfilling, and the fill pump assembly is an example of a simple and inexpensive apparatus for filling the infusor pump.

It will also be appreciated that the squeeze fill embodiment of FIG. 1 could be utilized with this disconnect infusion pump of FIGS. 9 and 10, instead of the separate pump 180 with actuator 190-200. The bag 182 could be sized to precisely fill the unit 144, which could be accommodated in the spherical chamber 12. The unit 10 would be made to open to enable removal of the infusor 144 if desired. It could also be retained in the housing as in the FIG. 1 embodiment.

While we have illustrated and described our invention by means of specific embodiments, it is to be understood that numerous changes and modifications may be made therein without departing from the spirit and scope of the invention as defined in the appended claims.

We claim:

1. An apparatus for dispensing a liquid under pressure at a substantially constant flow rate over a period of time comprising:
   a housing having a first chamber for containing a holding reservoir and a second chamber for containing a pressure reservoir;
   said second chamber being a substantially spherical chamber and an opening into said spherical chamber;

an elongated support member disposed in said spherical chamber and having an end disposed at said opening;

elastic means mounted on said support member in said spherical chamber for defining a pressure reservoir for holding a liquid in a pressurized state for dispensing therefrom;

inlet means for introducing a liquid into said pressure reservoir;

outlet means for dispensing liquid from said pressure reservoir to a selected site;

a holding reservoir in said first chamber for containing a predetermined quantity of a liquid in a non-pressurized state to be dispensed;

means for connecting said holding reservoir to said pressure reservoir for enabling the transfer of said liquid thereto;

said holding reservoir is formed of a pliable plastic material having a neck and an opening in said neck for transferring said liquid to said pressure reservoir; and means in said first chamber for collapsing said holding reservoir comprising opposed moveable walls moveable toward one another for forcing liquid from said holding reservoir to said pressure reservoir.

2. An apparatus for dispensing a liquid under pressure according to claim 1 wherein:

said support member is an elongated generally cylindrical mandrel mounted in said housing and having opposite ends exposed to the exterior of said housing, an inlet port in one end of said mandrel, and an outlet port in the other end of said mandrel; and said elastic sleeve is sealingly clamped at opposite ends thereof around opposite ends of said mandrel.

3. An apparatus for dispensing a liquid under pressure at a substantially constant flow rate over a period of time comprising:

a housing having a substantially spherical chamber and an opening into said chamber;

an elongated support member disposed in said chamber and having an end disposed at said opening;

elongated elastic sleeve means mounted in non-stretched surface contact and sealingly secured at fixed space longitudinal positions on said support member in said chamber for defining a substantially zero non-pressurized volume pressure reservoir for holding a liquid in a pressurized state for dispensing therefrom, said elastic means comprises a first elastic sleeve mounted on said support member, and a second elastic sleeve mounted over said first elastic sleeve so that said sleeves fold over onto the ends thereof when being filled;

inlet means for introducing a liquid into said elastic pressure reservoir; and outlet means for dispensing liquid from said pressure reservoir to a selected site.

4. An apparatus for dispensing a liquid under pressure at a substantially constant flow rate over a period of time comprising:

a housing having a substantially spherical chamber and an opening into said chamber;

an elongated support member disposed in said chamber and having an end disposed at said opening, said support member is an elongated substantially cylindrical member extending substantially through said housing;

elongated elastic sleeve means mounted in non-stretched surface contact and sealingly secured at fixed spaced longitudinal positions on said support member in said chamber for defining a substantially zero non-pressurized volume pressure reservoir for holding a liquid in a pressurized state for dispensing therefrom, said elastic means comprises a plurality of elastic sleeves extending over and along said support member and sealingly clamped thereto at opposite ends thereof so that said sleeves fold over onto the ends thereof when inflated;

inlet means for introducing a liquid into said elastic pressure reservoir; and outlet means for dispensing liquid from said pressure reservoir to a selected site.

5. An apparatus for dispensing a liquid under pressure at a predetermined substantially constant flow rate over a period of time comprising:

a housing having a substantially spherical chamber;

an elongated support member disposed in and extending through said chamber;

an elastic sleeve mounted on said support member in non-stretched surface contact and sealingly secured at fixed spaced longitudinal positions thereon in said chamber for defining a pressure reservoir for holding a liquid in a pressurized state for dispensing therefrom;

inlet means in said support member for introducing a liquid into said elastic sleeve; and outlet means in said support member for conveying a liquid from said pressure chamber to a selected site.

6. An apparatus for dispensing a liquid under pressure according to claim 5 wherein:

said support member is an elongated generally cylindrical mandrel mounted in said housing and having opposite ends exposed to the exterior of said housing, said inlet means comprises an inlet port in one end of said mandrel, and said outlet means comprises an outlet port in the other end of said mandrel; and said elastic sleeve is sealingly clamped at opposite ends thereof around opposite ends of said mandrel.

7. An apparatus for dispensing a liquid under pressure according to claim 6 further comprising:

a holding reservoir for containing a predetermined quantity of a liquid in a non-pressurized state to be dispensed;

means for connecting said holding reservoir to said pressure reservoir for enabling the transfer of said liquid thereto; and means for forcing liquid from said holding reservoir to said pressure reservoir.

8. An apparatus for dispensing a liquid under pressure according to claim 7 wherein said means for forcing said liquid from said holding reservoir comprises:

a pump apparatus comprising an elongated elastic cylindrical member defining a normally expanded collapsible chamber having walls of sufficient strength to spring back to its cylindrical configuration and draw liquid from said holding reservoir, an inlet having check valve means therein connected to said holding reservoir and an outlet having check valve means therein connected to said pressure reservoir; and means for selectively collapsing said elastic cylindrical member for transferring said liquid to said pressurized reservoir.

9. An apparatus for dispensing a liquid under pressure at a predetermined substantially constant flow rate over a period of time comprising:
- a housing having a first chamber for containing a holding reservoir and a second substantially spherical chamber for containing said pressure reservoir;
- an elongated support member disposed in and extending through said spherical chamber;
- an elastic sleeve mounted on said support member in said spherical chamber for defining a pressure reservoir for holding a liquid in a pressurized state for dispensing therefrom;
- inlet means in said support member for introducing a liquid into said elastic sleeve;
- outlet means in said support member for conveying a liquid from said pressure chamber to a selected site;
- said support member is an elongated generally cylindrical mandrel mounted in said housing and having opposite ends exposed to the exterior of said housing, said inlet means comprises an inlet port in one end of said mandrel, and said outlet means comprises an outlet port in the other end of said mandrel;
- said elastic sleeve is sealingly clamped at opposite ends thereof around opposite ends of said mandrel;
- means for connecting said holding reservoir to said pressure reservoir for enabling the transfer of said liquid thereto;
- a holding reservoir formed of a pliable plastic material for containing a predetermined quantity of a liquid in a non-pressurized state to be dispensed and having a neck and an opening in said neck for transferring said liquid to said pressure reservoir; and
- means in said first chamber for collapsing said holding reservoir comprising opposed moveable walls moveable toward one another for forcing liquid from said holding reservoir to said pressure reservoir.

10. An apparatus for dispensing a liquid under pressure at a substantially constant flow rate over a period of time comprising:
- a housing having a first chamber for containing a holding reservoir and a second chamber for containing a pressure reservoir;
- a pliable non-pressurized holding reservoir disposed in said first chamber for containing a predetermined quantity of liquid to be dispensed;
- an expansible elastic pressure reservoir in said second chamber for holding said liquid under pressure during dispensing thereof;
- means connecting said holding reservoir to said pressure reservoir for enabling the transfer of said liquid thereto;
- means for collapsing said holding reservoir for forcing liquid therein to said pressure reservoir; and
- discharge means for conveying a liquid from said pressure reservoir to a selected site.

11. An apparatus for dispensing a liquid under pressure according to claim 10 wherein:
said housing is formed of a pair of opposed complementary shell members pivotally connected together at one end and includes closely spaced opposed walls defining said means for collapsing said pressure reservoir.

12. An apparatus for dispensing a liquid under pressure according to claim 11 wherein:
said pressure reservoir is an elastic sleeve stretched over a mandrel.

13. An apparatus for dispensing a liquid under pressure according to claim 12 wherein:
said pressure reservoir is stretched over a generally cylindrical mandrel.

14. An apparatus for dispensing a liquid under pressure according to claim 12 wherein:
said pressure reservoir is stretched over a generally flat rectangular mandrel.

15. An apparatus for dispensing a liquid under pressure according to claim 13 wherein:
said second chamber is spherically shaped to accommodate the expansion of said pressure reservoir.

16. An apparatus for dispensing a liquid under pressure according to claim 14 wherein:
said second chamber is rectangularly box shaped to accommodate the expansion of said pressure reservoir.

* * * * *